United States Patent [19]

Hassall et al.

[11] Patent Number: 4,623,639

[45] Date of Patent: Nov. 18, 1986

[54] PEPTIDE DERIVATIVES

[75] Inventors: Cedric H. Hassall, Harpenden; William H. Johnson, Hitchin; Noel A. Roberts, Harpenden, all of United Kingdom

[73] Assignee: Hoffmann-La Roche Inc., Nutley, N.J.

[21] Appl. No.: 628,070

[22] Filed: Jul. 5, 1984

[30] Foreign Application Priority Data

Jul. 12, 1983 [GB] United Kingdom ................. 8318855
May 8, 1984 [GB] United Kingdom ................. 8411635

[51] Int. Cl.⁴ ........................ A61K 37/64; C07K 5/08
[52] U.S. Cl. ....................................... 514/18; 530/331

[58] Field of Search ................... 260/112.5 R; 514/19, 514/18

[56] References Cited

PUBLICATIONS

Hassall et al., *FEBS Lett.*, 183(2), 201-5 (1985).

*Primary Examiner*—Delbert R. Phillips
*Attorney, Agent, or Firm*—Jon S. Saxe; George M. Gould; Norman C. Dulak

[57] ABSTRACT

The present invention provides for peptide derivatives, a process for their manufacture and pharmaceutical preparations containing the same. The invention is also concerned with novel intermediates used in the manufacture of said derivatives.

16 Claims, No Drawings

PEPTIDE DERIVATIVES

SUMMARY OF THE INVENTION

Compounds of the formula

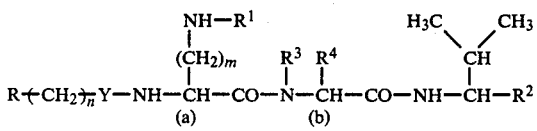

wherein R represents a cyclic hydrocarbon group containing from 6 to 12 carbon atoms, $R^1$ represents an acyl group derived from an aliphatic or aromatic dicarboxylic acid, which is optionally substituted by an amino group or by one or more hydroxy groups, or from a uronic acid, $R^2$ represents a hydrogen atom or a formyl group, $R^3$ represents a hydrogen atoms and $R^4$ represents a methyl group or $R^3$ and $R^4$ together represent a trimethylene group, Y represents a carbonyl, sulphonyl or methylene group, m stands for an integer of 2 to 6 and n stands for zero, 1 or 2 and wherein the configuration at the carbon atoms designated as (a) and (b) is L, and pharmaceutically acceptable salts thereof are described. These compounds and salts are useful in the treatment of degenerative diseases (e.g. emphysema) associated with the action of elastase-like enzymes and in the treatment of inflammatory conditions in which elastase-like enzymes act as mediators of inflammation.

DETAILED DESCRIPTION OF THE INVENTION

The peptide derivatives provided by the present invention are compounds of the general formula

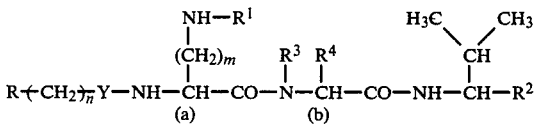

wherein R represents a cyclic hydrocarbon group containing from 6 to 12 carbon atoms, $R^1$ represents an acyl group derived from an aliphatic or aromatic dicarboxylic acid, which is optionally substituted by an amino group or by one or more hydroxy groups, or from a uronic acid, $R^2$ represents a hydrogen atom or a formyl group, $R^3$ represents a hydrogen atom and $R^4$ represents a methyl group or $R^3$ and $R^4$ together represent a trimethylene group, Y represents a carbonyl, sulphonyl or methylene group, m stands for an integer of 2 to 6 and n stands for zero, 1 or 2 and wherein the configuration at the carbon atoms designated as (a) and (b) is L, and pharmaceutically acceptable salts thereof.

The cyclic hydrocarbon group denoted by R herein can have a wide variety of meanings. For example, it can be a phenyl group or a phenyl group carrying one or more alkyl groups containing up to 4 carbon atoms (e.g. methyl, ethyl, n-propyl, isopropyl, n-butyl, isobutyl etc), with the proviso that the total number of carbon atoms in such an alkyl-substituted phenyl group does not exceed 12. Examples of such alkyl-substituted phenyl groups are o-tolyl, m-tolyl, p-tolyl, 2,4-dimethylphenyl etc. A further example of a cyclic hydrocarbon group denoted by R is a phenyl group carrying a phenyl substituent as in the case of 4-biphenylyl. Again, for example, R can be a fused cyclic hydrocarbon group such as naphthyl, tetrahydronaphthyl, decahydronaphthyl, indanyl etc. Yet again, for example, R can be a monocyclic or bridged cycloalkyl group, particularly cyclooctyl, cyclodecyl, adamantyl, bicycloheptyl and the like.

When $R^1$ represents an acyl group derived from an aliphatic dicarboxylic acid, optionally substituted as hereinbefore defined, this group can be derived from a saturated or unsaturated aliphatic dicarboxylic acid such as, for example, from succinic acid, glutaric acid, adipic acid, glutamic acid, aspartic acid, $\alpha$-amino dipic acid, malic acid, tartaric acid, fumaric acid and the like. Examples of acyl groups $R^1$ derived from an aromatic dicarboxylic acid are acyl groups derived from a benzenedicarboxylic acid such as phthalic acid, isophthalic acid, terephthalic acid etc or from a naphthalenedicarboxylic acid such as 1,5-naphthalenedicarboxylic acid, 1,8-naphthalenedicarboxylic acid etc. Examples of acyl groups $R^1$ derived from an uronic acid are the acyl groups derived from D-glucuronic acid and D-galacturonic acid.

When $R^2$ in formula I represents a formyl group the configuration at the carbon atom to which this groups is attached can be D or L. The present invention includes within its scope such D- and L-compounds as well as mixtures thereof. D or L as used herein is meant to represent, respectively, dextro and levo or (+) and (−) configuration as is commonly accepted by the art.

Compounds of formula I can form pharmaceutically acceptable salts with bases; for example, alkali metal salts such as the sodium or potassium salt and alkaline earth metal salts such as the calcium and magnesium salt. Compounds of formula I which contain a free amino group can form pharmaceutically acceptable salts with acids. These acids can be inorganic acids such as hydrohalic acids (e.g. hydrochloric acid or hydrobromic acid), sulphuric acid, phosphoric acid, nitric acid etc or organic acids such as acetic acid, maleic acid, fumaric acid, tartaric acid, citric acid, methanesulphonic acid etc.

Preferred compounds of formula I provided by the present invention are those in which, independently of one another, R represents a monocyclic or bridged cycloalkyl group containing from 6 to 12 carbon atoms, particularly adamantyl, $R^1$ represents an acyl group derived from an unsubstituted saturated aliphatic dicarboxylic acid containing up to 6 carbon atoms, particularly succinyl or adipolyl, or from an unsubstituted benzenedicarboxylic acid, particularly 4-carboxybenzoyl, $R^2$ represents a formyl group, Y represents a sulphonyl group, m stands for 4 and n stands for zero.

Especially preferred compounds of formula I are:
$N^\alpha$-(1-adamantylsulphonyl)-$N^\epsilon$-succinyl-L-lysyl-L-prolyl-L-valinal
$N^\alpha$-(1-adamantylsulphonyl)-$N^\epsilon$-(4-carboxybenzoyl)-L-lysyl-L-prolyl-L-valinal and
$N^\alpha$-(1-adamantylsulphonyl)-$N^\epsilon$-(4-carboxybenzoyl)-L-lysyl-L-alanyl-L-valinal.

Examples of other compounds of formula I are:
$N^\alpha$-(1-adamantylethyl)-$N^\epsilon$-succinyl-L-lysyl-L-proline isobutylamide,
$N^\alpha$-(6,6-dimethylbicyclo[3.1.1]heptylethyl)-$N^\epsilon$-($\gamma$-glutamyl)-L-lysyl-L-proline isobutylamide, N$^\alpha$-(1-adamantaneacetyl)-N$^\epsilon$-succinyl-L-lysyl-L-proline isobutylamide,
N$^\alpha$-(1-adamantylsulphonyl)-N$^\epsilon$-succinyl-L-lysyl-L-alanylvalinal,
N$^\alpha$-(1-adamantylsulphonyl)-N$^\epsilon$-(2-carboxybenzoyl)-L-lysyl-L-prolylvalinal and
N$^\alpha$-(1-adamantylsulphonyl)-N$^\epsilon$-adipolyl-L-lysyl-L-prolylvalinal.

According to the process provided by the present invention, the compounds of formula I hereinbefore and pharmaceutically acceptable salts thereof are manufactured by (a) reacting a compound of the general formula

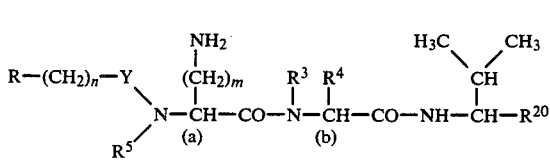

wherein R, R$^3$, R$^4$, Y, m and n have the significance given earlier, the configuration at the carbon atoms designated as (a) and (b) is as given earlier, R$^5$ represents a hydrogen atom when Y represents a carbonyl or sulphonyl group or represents a protecting group when Y represents a methylene group and R$^{20}$ represents a hydrogen atom or a protected formyl group, with a reactive derivative of an acid of the general formula $$HO-R^{10} \qquad \text{III}$$

wherein R$^{10}$ has the same significance as R$^1$ above, but wherein any carboxy, amino or hydroxy group therein is in protected form,
and, where required, cleaving off any protecting group(s) present in the reaction product, or (b) for the manufacture of a compound of formula I in which R$^1$ represents a 2-carboxybenzoyl group, treating a compound of the general formula

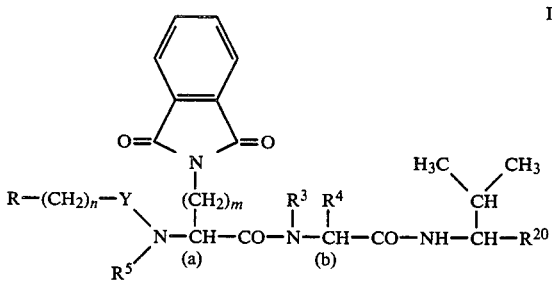

wherein R, R$^3$, R$^4$, R$^5$, R$^{20}$, Y, m and n have the significance given earlier and the configuration at the carbon atoms designated as (a) and (b) is as given earlier, with an alkali metal hydroxide and, where required, cleaving off any protecting group(s) present in the reaction product, and (c) in either case, if desired, converting a compound of formula I obtained into a pharmaceutically acceptable salt.

The protecting group denoted by R$^5$ in formulae II and IV can be a conventional protecting group such as, for example, a tert.butoxycarbonyl, benzyloxycarbonyl, formyl, trityl, trifluoroacetyl, 2-(biphenylyl)-isopropoxycarbonyl or like group. Preferably, R$^5$ represents a benzyloxycarbonyl group.

A protected formyl group denoted by R$^{20}$ in formulae II and IV is preferably formyl protected in the form of the dimethyl or diethyl acetal, but it can also be formyl protected in the form of an oxime, semicarbazide etc.

A carboxy, amino or hydroxy group present in R$^{10}$ in an acid of formula III can be protected in a conventional manner. For example, a carboxy group can be protected in the form of a readily cleavable ester such as the methyl, ethyl, tert.butyl, benzyl or like ester. Again, for example, an amino group can be protected with a protecting group of the kind mentioned earlier in connection with R$^5$ in formula II. Yet again, for example, a hydroxy group can be protected in the form of a readily cleavable ether such as the tert.butyl or tetrahydropyranyl ether or in the form of a readily cleavable ester such as an ester derived from an alkanecarboxylic acid (e.g. acetic acid etc).

The reactive derivative of an acid of formula III can be, for example, an acid halide (e.g. the acid chloride), an acid anhydride, an acid azide, an active amide (e.g. an amide with pyrazole, imidazole etc, a mixed carbonic anhydride or an active ester (e.g. the cyanomethyl, 4-nitrophenyl or N-hydroxysuccinimide ester).

The reaction of a compound of formula II with a reactive derivative of an acid of formula III in accordance with embodiment (a) of the process can be carried out in a manner known per se. The reaction is conveniently carried out in an inert organic solvent such as a halogenated hydrocarbon e.g. methylene chloride, chloroform etc.), an ether (e.g. tetrahydrofuran, dioxan etc), an ester (e.g. ethyl acetate etc), acetonitrile, dimethylformamide, dimethylacetamide etc or in a mixture of these solvents. It is convenient to carry out the reaction at a temperature between about $-20°$ C. and about $+40°$ C., especially between about $-10°$ C. and about $+30°$ C., and particularly between about $0°$ C. and room temperature. The reaction is conveniently carried out in the presence of a base such as a tertiary organic amine (e.g. triethylamine, N-methylmorpholine, N-ethylmorpholine etc) or an alkali metal carbonate (e.g. sodium bicarbonate etc). In certain circumstances it can be expedient to carry out this reaction in situ, i.e. without isolating the compound of formula II from the medium in which it is prepared.

After the reaction of a compound of formula II with a reactive derivative of an acid of formula III any protecting group or groups present in the reaction product is/are cleaved off. The cleavage of the protecting group(s) can be carried out in a manner known per se. Protecting groups which are cleavable by acidic hydrolysis can be removed, for example, by treatment with an inorganic acid such as hydrochloric acid, with a suitable alkanecarboxylic acid (e.g. acetic acid) which, if desired, can be halogenated (e.g. trifluoroacetic acid), or with a sulphonic acid such as toluene-4-sulphonic acid. Protecting groups which are cleavable by basic hydrolysis can be removed, for example, by treatment with an aqueous alkali metal hydroxide such as aqueous sodium hydroxide. Protecting groups which are cleavable by hydrogenolysis can be removed, for example, using hydrogen in the presence of a suitable catalyst such as palladium etc. When R$^{20}$ represents a protected formyl group, this can be converted into the formyl group according to methods known per se. For example, when R$^{20}$ represents a formyl group protected in the form of the dimethyl or diethyl acetal, the formyl group can be regenerated by treatment with, for example, an alkanesulphonic acid such as methanesulphonic acid, an aromatic sulphonic acid such as toluene-4-sulphonic acid, trifluoroacetic acid, a strong sulphonic acid resin such as Amberlyst 15, hydrochloric acid or the like.

When the product obtained by reacting a compound of formula II with a reactive derivative of an acid of formula III contains two or more protecting groups, these groups are preferably of a kind which can be cleaved off using one and the same method. Accordingly, the protecting groups in the starting materials used in the process are preferably chosen with this in mind. Alternatively, of course, the protecting groups can be of a kind which are cleaved off using different methods, in which case the cleavage of such protecting groups is carried out stepwise.

The treatment of a compound of formula IV with an alkali metal hydroxide in accordance with embodiment (b) of the process results in the opening of the $N^\epsilon$-phthaloyl group with the formation of a 2-carboxybenzoyl group. Conveniently, the reaction is carried out in aqueous-alcoholic solution such as aqueous-methanolic solution. Sodium hydroxide is the preferred alkali metal hydroxide. The reaction is preferably carried out at room temperature.

The removal of any protecting group or groups present in the product obtained after treating a compound of formula IV with an alkali metal hydroxide can be carried out in the same manner as described earlier in connection with the removal of any protecting group or groups from the product obtained by reacting a compound of formula II with a reactive derivative of an acid of formula III.

Compounds of formula I can be converted into pharmaceutically acceptable salts by treatment with a base and compounds of formula I which contain a free amino group can be converted into pharmaceutically acceptable acid addition salts by treatment with an acid. These treatments can be carried out in a conventional manner.

The compounds of formula II used as starting materials in the process provided by the present invention are novel and also form an object of the present invention. They can be prepared by converting the protected amino group denoted by $R^6$ in a compound of the general formula

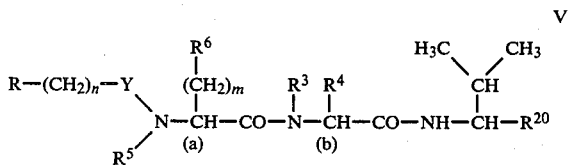

wherein R, $R^3$, $R^4$, $R^5$, $R^{20}$, Y, m and n have the significance given earlier, $R^6$ represents a protected amino group and the configuration at the carbon atoms designated as (a) and (b) is as given earlier,
into the amino group.

The protected amino group denoted by $R^6$ in a compound of formula V can be an amino group carrying a conventional protecting group as mentioned earlier in connection with $R^5$ or, preferably, a phthalimido group. When $R^6$ represents a phthalimido group, it will be appreciated that the compound of formula V corresponds to a compound of formula IV.

The conversion of the protected amino group denoted by $R^6$ in a compound of formula V into the amino group can be carried out in a known manner; for example, as described earlier or, when the protected amino group is phthalimido, by treatment with hydrazine in a conventional manner. It will be appreciated that, when more than one protecting group is present in a compound of formula V, these groups will be chosen so that only the protecting group present on $R^6$ is removed and that other protecting groups present in the molecule are not affected.

The compounds of formula V hereinbefore which are novel and form a further object of the present invention, can be prepared according to various methods.

According to one method, compounds of formula V can be prepared by reacting a compound of the general formula

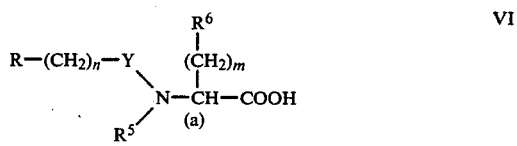

wherein R, $R^5$, $R^6$, Y, m and n have the significance given earlier and the configuration at the carbon atom designated as (a) is as given earlier,
with a compound of the general formula

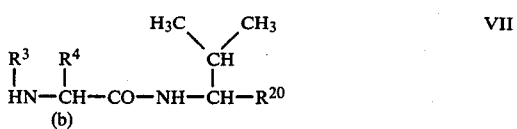

wherein $R^3$, $R^4$ and $R^{20}$ have the significance given earlier and the configuration at the carbon atom designated as (b) is as given earlier,
in a manner known per se.

According to another method, compounds of formula V can be prepared by reacting a compound of the general formula

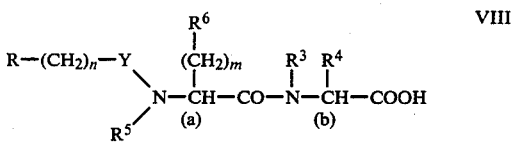

wherein R, $R^3$, $R^4$, $R^5$, $R^6$, Y, m and n have the significance given earlier and the configuration at the carbon atoms designated as (a) and (b) is as given earlier,
with a compound of the general formula

wherein $R^{20}$ has the significance given earlier,
in a manner known per se.

According to a further method, compounds of formula V in which Y represents a carbonyl or sulphonyl group can be prepared by reacting a compound of the general formula

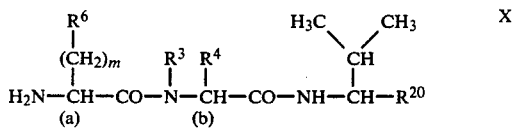

wherein $R^3$, $R^4$, $R^6$, $R^{20}$ and m have the significance given earlier and the configuration at the carbon atoms designated as (a) and (b) is as given earlier, with a compound of the general formula $$R—(CH_2)_n—Y^1—X \qquad XI$$

wherein R and n have the significance given earlier, X represents a chlorine or bromine atom and $Y^1$ represents a carbonyl group, a sulphonyl group (except when R represents adamantyl) or a sulphinyl group (when R represents adamantyl),
in a known manner and oxidizing a compound obtained in which $Y^1$ represents a sulphinyl group to a corresponding compound of formula V in which Y represents a sulphonyl group, likewise in a known manner.

According to a still further method, the compounds of formula V in which Y represents a methylene group can be prepared by reductively alkylating a compound of formula X hereinbefore with an aldehyde of the general formula $$R—(CH_2)_n—CHO \qquad XII$$

wherein R and n have the significance given earlier, in a conventional manner.

Compounds of formula VI hereinbefore can be prepared either by reacting an appropriate compound of the general formula

wherein $R^6$ and m have the significance given earlier and the configuration at the carbon atom designated as (a) is as given earlier,
with a compound of the general formula $$R—(CH_2)_n—Y^2—X \qquad XIV$$

wherein R, X and n have the significance given earlier and $Y^2$ has the same significance as Y hereinbefore, but represents a carbonyl, methylene or sulphinyl group when R represents adamantyl,
and oxidizing a compound obtained in which $Y^2$ represents a sulphinyl group to a corresponding compound of formula VI in which Y represents a sulphonyl group, or by subjecting a compound of formula XIII to reductive alkylation with an aldehyde of formula XII hereinbefore followed by introduction of the protecting group $R^5$.

The compounds of formulae VII, IX, XI, XII, XIII and XIV hereinbefore are either known compounds or analogues of known compounds.

Compounds of formula VIII hereinbefore can be prepared, for example, by reacting a compound of formula VI hereinbefore with a L-proline or L-alanine ester (e.g. the methyl, ethyl, tert.butyl or benzyl ester) and subsequently cleaving off the ester protecting group.

Compounds of formula X hereinbefore can be prepared, for example, by reacting a compound of formula VII hereinbefore with a compound corresponding to formula XIII hereinbefore, but in which the amino group therein carries a protecting group $R^5$ and subsequently cleaving off the protecting group denoted by $R^5$ in the reaction product.

The reactive derivatives of the acids of formula III used as starting materials in the process provided by the present invention are known substances.

The compounds of formula I and their pharmaceutically acceptable salts can be used in the treatment of degenerative diseases such as emphysema associated with the action of elastase-like enzymes. They can also be used for the treatment of inflammatory conditions in which elastase-like enzymes act as mediators of inflammation.

The pharmacological activity of the compounds of this invention is demonstrated by the following test:

ASSAY OF THE INHIBITION OF HUMAN GRANULOCYTE ELASTASE TEST METHOD

This assay is based on the method of J. Bieth, B. Spiess and C. G. Wermuth, Biochem. 11, (1974), 350. Succinyl $(Ala)_3$-p-nitroanilide (20 μl of a 125 mM solution in N-methylpyrrolidone) was diluted in buffer (3 ml, 0.2M Tris HCl, pH 8.0) and warmed to 37° C. Human granulocyte elastase (4 μg in 20 μl of buffer) was added to initiate the reaction, which was terminated after 1 hour at 37° C. by the addition of glacial acetic acid (100 μl). The p-nitroaniline released was determined by measuring the extinction of the solution at 410 nm by means of a spectrophotometer. The compounds of the present invention, in 50 μl of methanol, were added to the buffered substrate prior to the addition of the human granulocyte elastase and the substrate cleavage rate was compared with solvent controls. The concentration of compound of the present invention required to give 50% inhibition was determined.

The results are compiled in the following Table:

TABLE

| Compound of the present invention | $IC_{50}$ |
|---|---|
| $N^\alpha$—(1-Adamantylsulphonyl)-$N^\epsilon$—succinyl-L-lysyl-L-prolyl-L-valinal. | $8 \times 10^{-8}$ M |
| $N^\alpha$—(1-Adamantylethyl)-$N^\epsilon$—succinyl-L-lysyl-L-proline isobutylamide | $4.5 \times 10^{-6}$ M |
| $N^\alpha$—(6,6-Dimethylbicyclo-[3.3.1]heptylethyl)-$N^\epsilon$—(γ-glutamyl)-L-lysyl-L-proline isobutylamide | $1.6 \times 10^{-5}$ M |
| $N^\alpha$—(1-Adamantylsulphonyl)-$N^\epsilon$—(2-carboxybenzoyl)-L-lysyl-L-prolylvalinal | $9 \times 10^{-8}$ M |
| $N^\alpha$—(1-Adamantylsulphonyl)-$N^\epsilon$—succinyl-L-lysyl-L-alanylvalinal | $1.2 \times 10^{-7}$ M |
| $N^\alpha$—(1-Adamantylsulphonyl)-$N^\epsilon$—(4-carboxybenzoyl)-L-lysyl-L-prolyl-L-valinal | $6 \times 10^{-8}$ M |
| $N^\alpha$—(1-Adamantylsulphonyl)-$N^\epsilon$—adipoyl-L-lysyl-L-prolylvalinal | $8 \times 10^{-8}$ M |
| $N^\alpha$—(1-Adamantylsulphonyl)-$N^\epsilon$—(4-carboxybenzoyl)-L-lysyl-L-alanyl-L-valinal | $5 \times 10^{-8}$ M |

The toxicity of the compounds of this invention is determined using the following test:

MAXIMUM TOLERATED DOSE TEST TEST METHOD

This test determines the maximum acute dose of a compound of this invention which causes no gross behavioural effects.

Groups of 3 male mice are administered 400 mg/kg and 100 mg/kg of a compound of this invention subcutaneously, intravenously or intraperitoneally. The mice are observed periodically during the 6 hours after the administration and 24 hours after the administration. Evidence of stimulation, sedation, loss of righting reflex, convulsions, tremor, death and other gross effects are noted. If effects are observed, the compound is tested at lower dosages in order to determine the no gross effect level. The results are expressed as the maximum dose administered in mg/kg which causes no gross behavioural effects.

In the case of the compounds of the present invention, no behavioural effects were observed:

(1) with $N^\alpha$-(1-adamantylsulphonyl)-$N^\epsilon$-succinyl-L-lysyl-L-prolyl-L-valinal at a dosage of 400 mg/kg subcutaneously and a dosage of 100 mg/kg intravenously;

(2) with $N^\alpha$-(1-adamantylethyl)-$N^\epsilon$-succinyl-L-lysyl-L-proline isobutylamide at a dosage of 50 mg/kg intraperitoneally;

(3) with $N^\alpha$-(1-adamantylsulphonyl)-$N^\epsilon$-(4-carboxybenzoyl)-L-lysyl-L-alanyl-L-valinal and with $N^\alpha$-(1-adamantylsulphonyl)-$N^\epsilon$-(4-carboxybenzoyl)-L-lysyl-L-prolyl-L-valinal, in each case at a dosage of 400 mg/kg subcutaneously, 100 mg/kg intraperitoneally and 100 mg/kg intravenously.

The compounds of formula I and their pharmaceutically acceptable salts can be used as medicaments in the form of pharmaceutical preparations which contain them in asssociation with a compatible pharmaceutical carrier material. This carrier material can be an organic or inorganic carrier material which is suitable for enteral or parenteral administration such as water, lactose, starch, magnesium stearate, talc, gum arabic, gelatine, polyalkylene glycols, petroleum jelly etc. The pharmaceutical preparations can be made up in a solid form (e.g. as tablets, powders, dragees, suppositories, capsules etc) or in a liquid form (e.g. as solutions, emulsions, suspensions etc). The pharmaceutical preparations are, however, preferably provided in the form of an aerosol which conveniently contains, in addition to the propellant, a solvent such as ethanol.

If necessary, the pharmaceutical preparations provided by the present invention can be subjected to conventional pharmaceutical operations such as sterilization and the like and they can also contain conventional pharmaceutical adjuvants such as preserving agents, stabilizing agents, wetting agents, salts for varying the osmotic pressure etc. The present pharmaceutical preparations may also contain other therapeutically valuable substances.

The pharmaceutical preparations provided by the present invention can be manufactured by mixing a compound of formula I or a pharmaceutically acceptable salt thereof with a compatible pharmaceutical carrier material and bringing the mixture obtained into the desired pharmaceutical dosage form.

The compounds of formula I and their pharmaceutically acceptable acid addition salts may be administered to adults in a dosage range of from about 5 mg to 30 mg, preferably about 10 mg to 15 mg, per day. It will, of course, be appreciated that this dosage range is given by way of example only and that it can be varied upwards or downwards depending on factors such as the potency of the particular compound to be administered, the particular condition to be treated and the individual requirements of the patient as determined by the attending physician.

The following examples illustrate the present invention. The structure of the products was confirmed by NMR spectroscopy and mass spectroscopy.

EXAMPLE 1

(A) 4.55 g (0.0065 mol) of $N^\alpha$-(1-adamantylsulphonyl)-$N^\epsilon$-phthaloyl-L-lysyl-L-prolyl-L-valinal dimethyl acetal in 30 ml of ethanol and 0.94 ml of hydrazine hydrate were stirred at room temperature for 16 hours. The solution was filtered and the filtrate was evaporated. Traces of hydrazine hydrate were removed from the residue by two-fold evaporation with 20 ml of ethanol each time. The residue was then dissolved in ethanol, 0.9 ml of acetic acid was added and the solution was stirred for 20 minutes. The solvent was removed by evaporation and traces of acetic acid in the residue were removed by three-fold evaporation with 20 ml of ethanol each time. The residue was taken up in 20 ml of chloroform, the solution was stored at 0° C. for 0.5 hour, filtered and the filtrate was evaporated to give a foam. This foam was taken up in 15 ml of tetrahydrofuran, the solution was treated with 2.76 ml (0.0195 mol) of triethylamine and 1.3 g (0.013 mol) of succinic anhydride and the mixture was left to stand at room temperature for 16 hours. The solvent was removed by evaporation and the residue was dissolved in ethyl acetate/sodium bicarbonate solution. The aqueous layer was separated, extracted with ethyl acetate and acidified to pH 3–4 with dilute hydrochloric acid. The product was extracted with three 20 ml portions of chloroform. The chloroform extracts were washed with water, dried over magnesium sulphate and evaporated to give 3.9 g (89%) of $N^\alpha$-(1-adamantylsulphonyl)-$N^\epsilon$-succinyl-L-lysyl-L-propyl-L-valinal dimethyl acetal as a foam; Rf-value [chloroform/methanol/acetic acid/water (120:15:3:2)]: 0.52.

(B) 0.46 g (0.69 mmol) of $N^\alpha$-(1-adamantylsulphonyl)-$N^\epsilon$-succinyl-L-lysyl-L-prolyl-L-valinal dimethyl acetal in 25 ml of acetone was treated with 0.14 g of toluene-4-sulphonic acid at room temperature for 16 hours. The solvent was removed by evaporation, the residue was dissolved in 7 ml of chloroform, the solution was washed with water, dried over magnesium sulphate and evaporated to give a foam. Chromatography on 60 g of silica gel using chloroform/methanol/acetic acid/water (120:15:3:2) for the elution followed by lyophilization from acetic acid/water (1:4) yielded 0.13 g (30% of $N^\alpha$-(1-adamantylsulphonyl)-$N^\epsilon$-succinyl-L-lysyl-L-prolyl-L-valinal. Rf-value [chloroform/methanol/acetic acid/water (120:15:3:2)]: 0.32; $[\alpha]_D^{20} = -41.8°$ (c=0.25 in 50% acetic acid).

Analysis for $C_{30}H_{48}N_4O_8S$ (624.80): Calculated: C: 58.29; H: 7.89; N: 8.77%. Found: 56.20; H: 7.62; N: 8.54%. C: 56.23; H: 7.75; N: 8.52% (with 0.5 mol of $H_2O$ and 0.4 mol of $CH_3COOH$).

The $N^\alpha$-(1-adamantylsulphonyl)-$N^\epsilon$-phthaloyl-L-lysyl-L-prolyl-L-valinal dimethyl acetal used as the starting material in paragraph (A) was prepared as follows;

(a) 22.8 g (0.097 mol) of N-benzyloxycarbonyl-L-valinal were dissolved in 55 ml of dry methanol. The solution was treated with 10.8 g (0.102 mol) of trimethyl orthoformate and 0.3 g of toluene-4-sulphonic acid and the mixture was left to stand at room temperature for 16 hours. The solvents were removed by evaporation, the residue was dissolved in 150 ml of ethyl acetate and the solution was washed with 5% sodium bicarbonate solution and then with brine. After drying over magnesium sulphate and filtration, the solvent was removed by evaporation to yield 24.5 g (90%) of N-benzyloxycarbonyl-L-valinal dimethyl acetal as an oil; Rf-value [hexane/ethyl acetate (2:1)]: 0.69.

(b) 24.5 g (0.087 mol) of N-benzyloxycarbonyl-L-valinal dimethyl acetal were dissolved in 200 ml of methanol and the solution was hydrogenated for 2 hours in the presence of 0.5 g of 5% palladium/carbon. After removal of the catalyst by filtration, the solvent was removed by evaporation and the residue was dissolved in 250 ml of dichloromethane. The solution was washed with brine and dried over magnesium sulphate. The solution was then cooled to −20° C. and there were then added 21.8 g (0.087 mol) of N-benzyloxycarbonyl-L-proline followed by 19.8 g (0.096 mol) of N,N′-dicyclohexylcarbodiimide. The solution was stirred at −20° C. for 2 hours and left to stand at 4° C. for 64 hours. The separated N,N′-dicyclohexylurea was removed by filtration and the filtrate was evaporated. The residue was taken up in ethyl acetate, the solution was washed with sodium bicarbonate solution and brine, dried over magnesium sulphate and evaporated to give an oil. The product was purified by chromatography on 250 g of silica gel using ethyl acetate/hexane (1:1) for the elution. Evaporation of the solution yielded 21.9 g (67%) of N-benzyloxycarbonyl-L-prolyl-L-valinal dimethyl acetal; Rf-value (ethyl acetate): 0.63.

(c) 6.05 g (0.016 mol) of N-benzyloxycarbonyl-L-prolyl-L-valinal dimethyl acetal were dissolved in 60 ml of methanol and the solution was hydrogenated for 4 hours in the presence of 0.25 g of 5% palladium/carbon. After removal of the catalyst by filtration, the solvent was removed by evaporation and traces of methanol were removed from the residue by two-fold evaporation with 20 ml of toluene each time. A solution of the residue in 30 ml of dichloromethane was cooled to −20° C. and there were then added 6.9 g (0.0146 mol) of $N^\alpha$-(1-adamantylsulphonyl)-$N^\epsilon$-phthaloyl-L-lysine followed by 3.36 g (0.016 mol) of N,N′-dicyclohexylcarbodiimide. The mixture was stirred at −20° C. for 2 hours and left to stand at 4° C. for 16 hours. The separated N,N′-dicyclohexylurea was removed by filtration, the filtrate was washed with sodium bicarbonate solution and brine, dried over magnesium sulphate and evaporated to give an oil. The product was purified by chromatography on 100 g of silica gel using hexane/ethyl acetate (4:1) and then hexane/ethyl acetate (1:3) for the elution. Evaporation of the solvent yielded 5.5 g (54%) of $N^\alpha$-(1-adamantylsulphonyl)-$N^\epsilon$-phthaloyl-L-lysyl-L-prolyl-L-valinal dimethyl acetal; Rf-value (ethyl acetate): 0.57.

Analysis for $C_{36}H_{52}N_4O_8S$ (700.90): Calculated: C: 61.69; H: 7.48; N: 7.99%. Found: C: 61.48; H: 7.35; N: 7.91%.

The $N^\alpha$-(1-adamantylsulphonyl)-$N^\epsilon$-phthaloyl-L-lysine used in paragraph (c) was prepared as follows:

(a) 27.0 g (0.098 mol) of $N^\epsilon$-phthaloyl-L-lysine were suspended in 500 ml of dimethylformamide. 29.7 ml (0.235 mol) of N-ethylmorpholine and 32.2 g (0.147 mol) of 1-adamantanesulphinyl chloride were added and the mixture was stirred at room temperature for 16 hours. The solvent was removed by evaporation and the residue was dissolved in ethyl acetate/5% sodium bicarbonate solution. The aqueous layer was extracted with ethyl acetate and then acidified to pH 2 with concentrated hydrochloric acid. The oily product was extracted into ethyl acetate, whereupon some product crystallized out. The solid (mainly one diastereoisomer) was filtered off, washed with water and diethylether and dried in vacuo. The ethyl acetate solution was washed with water and brine, dried over magnesium sulphate and evaporated to dryness. Trituration with diethyl ether at 0° C. for 16 hours gave a solid which was filtered off, washed with diethyl ether and dried in vacuo. The resulting solid was combined with the solid obtained as described earlier, there being obtained 27.2 g (61%) of $N^\alpha$-(1-adamantylsulphinyl)-$N^\epsilon$-phthaloyl-L-lysine as a mixture of diastereoisomers; Rf-values [methanol/chloroform (1:9)]: 0.53 and 0.27.

(b) 27.2 g (0.059 mol) of N-(1-adamantylsulphinyl)-$N^\epsilon$-phthaloyl-L-lysine in 200 ml of glacial acetic acid were treated with 27 ml of 30% (wt/vol) hydrogen peroxide solution at 65° C. for 2 hours. The solution was cooled to room temperature, poured into 1.5 l of water and the product was extracted into two 200 ml of ethyl acetate. The organic solution was washed with three 100 ml portions of water and brine, dried over magnesium sulphate and evaporated to give an oil. Final traces of acetic acid were removed by two-fold evaporation with 50 ml of toluene each time. Drying in a high vacuum yielded 21.7 g (78%) of $N^\alpha$-(1-adamantylsulphonyl)-$N^\epsilon$-phthaloyl-L-lysine as a white foam; Rf-value [methanol/chloroform (1.19)]: 0.57; $[\alpha]_D^{20} = -14.8°$ (c=1% in dimethylformamide).

Analysis for $C_{24}H_{30}N_2O_6S$ (474.6): Calculated: C: 60.74; H: 6.37; N: 5.90%. Found: C: 60.19; H: 6.29; N: 5.99; $H_2O$: 1.42%. Water-free: C: 61.05; H: 6.21; N: 6.07%.

EXAMPLE 2

(A) 2.4 g (0.0034 mol) of $N^\alpha$-(1-adamantylethyl)-$N^\alpha$-benzyloxycarbonyl-$N^\epsilon$-tertbutoxycarbonyl-L-lysyl-L-proline isobutylamide were treated with 10 ml of 4M hydrogen chloride in ethyl acetate at room temperature for 0.5 hour. Dry diethyl ether was added and the white solid obtained was washed with diethyl ether and dried in the flask on a rotary evaporator. A solution of the solid in dimethylformamide was adjusted to pH 8 with N-ethylmorpholine, 0.68 g (0.0068 mol) of succinic anhydride was added and the pH of the resulting solution was held at 8 for 2 hours by the dropwise addition of N-ethylmorpholine. The solvent was removed by evaporation and the residue was dissolved in ethyl acetate/aqueous hydrochloric acid (pH 3). The organic layer was washed with water, the product was extracted into two 50 ml portions of 5% sodium bicarbonate solution and these solutions were combined and adjusted to pH 3 with 2M hydrochloric acid. The product was extracted into two 50 ml portions of ethyl acetate which were combined, washed with water and dried over magnesium sulphate. Evaporation of the solvent yielded 2.0 g (85%) of $N^\alpha$-(1-adamantylethyl)-$N^\alpha$-benzyloxycarbonyl-$N^\epsilon$-succinyl-L-lysyl-L-proline isobutylamide as a foam.

Analysis for $C_{39}H_{58}N_4O_7$ (694.92): Calculated: C: 67.41; H: 8.41; N: 8.06%. Found: C: 67.06; H: 8.24; N: 7.74%.

(B) 2.0 g (0.0029 mol) of $N^\alpha$-(1-adamantylethyl)-$N^\alpha$-benzyloxycarbonyl-$N^\epsilon$-succinyl-L-lysyl-L-proline isobutylamide were dissolved in 50 ml of methanol and the solution was hydrogenated for 3 hours in the presence of 0.2 g of 5% palladium/carbon. The catalyst was removed by filtration and the filtrate was evaporated to yield 1.6 g (98%) of $N^\alpha$-(1-adamantylethyl)-$N^\epsilon$-succinyl-L-lysyl-L-proline isobutylamide as a foam; $[\alpha]_D^{20} = -47.2°$ (c=1 in methanol).

Analysis for $C_{31}H_{52}N_4O_5$ (560.78): Calculated: C: 66.40; H: 9.35; N: 9.99%. Found: C: 66.52; H: 9.09; N: 9.80%.

The $N^\alpha$-(1-adamantylethyl)-$N^\alpha$-benzyloxycarbonyl-$N^\epsilon$-tert.butoxycarbonyl-L-lysyl-L-proline isobutylamide used as the starting material in paragraph (A) was prepared as follows:

(a) 35.6 g (0.143 mol) of N-benzyloxycarbonyl-L-proline were dissolved in 200 ml of tetrahydrofuran and the solution was cooled to −20° C. 18.1 ml (0.143 mol) of N-ethylmorpholine and 18.6 ml (0.143 mol) of isobutyl chloroformate were added and the mixture was stirred at −20° C. for 4 minutes. 14.2 ml (0.143 mol) of isobutylamine were added and the mixture was stirred at 0° C. for 2 hours and at room temperature for 16 hours. The solvent was removed by evaporation and the residue was dissolved in ethyl acetate. The solution obtained was washed with 5% citric acid solution, water, 5% sodium bicarbonate solution and brine, dried over magnesium sulphate and evaporated. Trituration of the resulting oil with petroleum ether (40°-60° C.) yielded 31.1 g (72%) of N-benzyloxycarbonyl-L-prolyl isobutylamide of melting point 84°-85° C.; $[\alpha]_D^{20} = -53.2°$ (c=1 in methanol).

Analysis for $C_{17}H_{24}N_2O_3$ (304.39): Calculated: C: 67.08; H: 7.95; N: 9.20%. Found: C: 66.92; H: 7.92; N: 9.07%.

(b) 31.1 g (0.102 mol) of N-benzyloxycarbonyl-L-proline isobutylamide were dissolved in 300 ml of dimethylformamide and the solution was hydrogenated for 16 hours in the presence of 3 g of 5% palladium/carbon. After removal of the catalyst by filtration the filtrate was cooled to 0° C. 49.1 g (0.101 mol) of $N^\alpha$-benzyloxycarbonyl-$N^\alpha$-tert.-butoxycarbonyl-L-lysine N-hydroxysuccinimide ester dissolved in 250 ml of dimethylformamide were added and the mixture was stirred at 0° C. for 1 hour and at room temperature for 16 hours. The solvent was removed by evaporation and the residue was dissolved in ethyl acetate/5% citric acid solution. The organic layer was washed with water, 5% sodium bicarbonate solution and brine, dried over magnesium sulphate and evaporated. Crystallization of the residue from diethyl ether/petroleum ether yielded 36.4 g (57%) of $N^\alpha$-benzyloxycarbonyl-$N^\epsilon$-tert.butoxycarbonyl-L-lysyl-L-proline isobutylamide of melting point 105°-107° C.

(c) A solution of 6.3 g (0.012 mol) of $N^\alpha$-benzyloxycarbonyl-$N^\epsilon$-tert.butoxycarbonyl-L-lysyl-L-proline isobutylamide in 100 ml of methanol was hydrogenated for 3 hours in the presence of 0.6 g of 5% palladium/carbon. A solution of 2.2 g (0.012 mol) of adamantane acetaldehyde in 5 ml of methanol was added via a septum cap and the hydrogenation was continued for 16 hours. The catalyst was removed by filtration and the filtrate was evaporated. A solution of the residue in 70 ml of diethyl ether was treated with 60 ml of water containing 2.5 g (0.025 mol) of potassium bicarbonate. 1.85 ml (0.023 mol) of benzyl chloroformate were added and the mixture was stirred vigorously for 1 hour. The organic solution was separated washed with 5% citric acid solution, water, 5% sodium bicarbonate solution and brine, dried over magnesium sulphate and evaporated to give a foam. Chromatography on 150 g of silica gel using n-hexane/ethyl acetate (2:1) yielded 4.4 g (53%) of $N^\alpha$-(1-adamantylethyl)-$N^\alpha$-benzyloxycarbonyl)-$N^\epsilon$-tert.butoxycarbonyl-L-lysyl-L-proline isobutylamide as a foam; Rf-value [n-hexane/ethyl acetate (2:1)]: 0.49.

EXAMPLE 3

(A) 3.8 g (0.0056 mol) of $N^\alpha$-(6,6-dimethylbicyclo-[3.1.1]heptylethyl)-$N^\alpha$-benzyloxycarbonyl-$N^\epsilon$-tert.butoxycarbonyl-L-lysyl-L-proline isobutylamide were dissolved in 5 ml of ethyl acetate and the solution was treated at room temperature for 50 minutes with 10 ml of 4M hydrochloric acid in ethyl acetate. Dry diethyl ether was added and the separated solid was washed with diethyl ether and dried in vacuo. The solid was then dissolved in 25 ml of dimethylformamide, the solution was cooled to 0° C. and neutralized with N-ethylmorpholine. 2.2 g (0.0055 mol) of $N^\alpha$-tert.-butoxycarbonyl-L-glutamic acid α-tert.butyl γ-N-hydroxysuccinimide ester were added and the mixture was left to stand at room temperature for 16 hours. The solvent was removed by evaporation and the residue was dissolved in ethyl acetate/water. The organic layer was washed with 5% citric acid solution, water, 5% sodium bicarbonate solution and brine, dried over magnesium sulphate and evaporated to give a foam. Chromatography on 150 g of silica gel using ethyl acetate for the elution yielded 2.75 g (57%) of $N^\alpha$-(6,6-dimethylbicyclo-[3.1.1]heptylethyl)-$N^\alpha$-benzyloxycarbonyl-$N^\epsilon$-(N-tert.butoxycarbonyl-L-glutamyl-α-tert.butyl ester)-L-lysyl-L-proline isobutylamide as a foam.

Analysis for $C_{48}H_{77}N_5O_9$ (868.18): Calculated: C: 66.41; H: 8.94; N: 8.07%. Found: C: 66.61; H: 8.85; N: 8.16%.

(B) 1.0 g (0.0012 mol) of $N^\alpha$-(6,6-dimethylbicyclo-[3.1.1]heptylethyl)-$N^\alpha$-benzyloxycarbonyl-$N^\epsilon$-(N-tert.butoxycarbonyl-L-glutamyl-α-tert.butyl ester)-L-lysyl-L-proline isobutylamine was dissolved in 1 ml of acetic acid, 3 ml of 45% hydrogen bromide in acetic acid were added and the mixture was stirred at room temperature for 0.5 hour. Dry diethyl ether was added and the separated white solid was washed with diethyl ether and dried in vacuo to yield 0.81 g (95%) of $N^\alpha$-(6,6-dimethylbicyclo-[3.1.1]heptylethyl)-$N^\epsilon$-(γ-glutamyl)-L-lysyl-L-proline isobutylamide dihydrobromide of melting point 198°-201° C.; $[\alpha]_D^{20} = -29.6°$ (c=1 in methanol).

Analysis for $C_{31}H_{55}N_5O_5 \cdot 2HBr$ (739.65): Calculated: C: 50.34; H: 7.77; N: 9.47%. Found: C: 50.52; H: 7.59; N: 9.47%.

The $N^\alpha$-(6,6-dimethylbicyclo-[(3.1.1]heptylethyl)-$N^\alpha$-benzyloxycarbonyl-$N^\epsilon$-tert.butoxycarbonyl-L-lysyl-L-proline isobutylamide used as the starting material in paragraph (A) can be prepared as follows:

In a manner analogous to that described in Example 3(c), from $N^\alpha$-benzyloxycarbonyl-$N^\epsilon$-tert.butoxycarbonyl-L-lysyl-L-proline isobutylamide and dihydronopal there was obtained N-(6,6-dimethylbicyclo-[3.1.1]heptylethyl)-$N^\alpha$-benzyloxycarbonyl-$N^\epsilon$-tert.butoxycarbonyl-L-lysyl-L-proline isobutylamide as a foam in a yield of 39%; Rf-value [methanol/chloroform (1:19)]: 0.82.

Analysis for $C_{39}H_{62}N_4O_6$ (682.95): Calculated: C: 68.59; H: 9.15; N: 8.20%. Found: C: 66.09; H: 8.83; N: 7.98%. C: 66.14; H: 8.80; N: 7.86% (with 0.25 mol of $CHCl_3$).

EXAMPLE 4

0.9 g (0.0015 mol) of $N^\alpha$-(1-adamantaneacetyl)-$N^\epsilon$-benzyloxycarbonyl-L-lysyl-L-proline isobutylamide were dissolved in 3 ml of acetic acid and 3 ml of 45% hydrogen bromide solution were added. After 1 hour, dry diethyl ether was added and the separated solid was filtered off, washed with diethyl ether and dried. The solid was taken up in 10 ml of dimethylformamide and the solution was treated with 0.41 ml (0.0033 mol) of N-ethylmorpholine and 0.3 g (0.003 mol) of succinic anhydride at room temperature for 16 hours. The solvent was removed by evaporation and the residue was dissolved in ethyl acetate/dilute hydrochloric acid (pH 3). The organic solution was extracted with two 15 ml portions of 5% sodium bicarbonate solution. Acidification to pH 3 followed by extraction into ethyl acetate, washing with water, drying over magnesium sulphate and evaporation gave the crude product. Chromatography on 10 g of silica gel using ethyl acetate containing 3% methanol for the elution gave 0.37 g (43%) of $N^\alpha$-(1-adamantaneacetyl)-$N^\epsilon$-succinyl-L-lysyl-L-proline isobutylamide as an oil; Rf-value [methanol/chloroform [3:97]]: 0.4.

Analysis for $C_{31}H_{49}N_4O_6$ (573.76): Calculated: C: 64.90; H: 8.61; N: 9.77%. Found: C: 62.53; H: 8.39; N: 9.19%. C: 62.44; H: 8.26; N: 9.33% (with 0.22 mol of $CHCl_3$).

The $N^\alpha$-(1-adamantaneacetyl)-$N^\epsilon$-benzyloxycarbonyl-L-lysyl-L-proline isobutylamide used as the starting material in the preceding paragraph was prepared as follows:

(a) 6.1 g (0.02 mol) of N-benzyloxycarbonyl-L-proline isobutylamide were stirred with 15 ml of 45% hydrogen bromide in acetic acid at room temperature for 1 hour. Dry diethyl ether was added, the resulting oil was washed with diethyl ether by decantation and dried on a rotary evaporator. The residue was dissolved in 50 ml of tetrahydrofuran, the solution was neutralized with N-ethylmorpholine and added to a mixed anhydride solution prepared by treating 7.6 g (0.02 mol) of $N^\alpha$-tert.butoxycarbonyl-$N^\epsilon$-benzyloxycarbonyl-L-lysine in 100 ml of tetrahydrofuran at $-20°$ C. with 2.54 ml (0.02 mol) of N-ethylmorpholine and 2.62 ml (0.02 mol) of isobutyl chloroformate and stirring the solution for 4 minutes before the addition.

The mixture was stirred at 0° C. for 2 hours, the solvent was removed by evaporation and the residue was dissolved in ethyl acetate/water. The organic solution was washed with 5% citric acid solution, water, 5% sodium bicarbonate solution and brine and then dried over magnesium sulphate. Evaporation of the solvent yielded 9.1 g (85%) of $N^\alpha$-tert.butoxycarbonyl-$N^\epsilon$-benzyloxycarbonyl-L-lysyl-L-proline isobutylamide as an oil; $R_f$-value [methanol/chloroform (1:9)]: 0.75

(b) 2.72 g (0.005 mol) of $N^\alpha$-tert.butoxycarbonyl-$N^\epsilon$-benzyloxycarbonyl-L-lysyl-L-proline isobutylamide were treated with 15 ml of 2.5M hydrogen chloride in ethyl acetate at room temperature for 0.75 hour. The solvent was removed by evaporation and the solid was washed with diethyl ether. The solid was taken up in 15 ml of dimethylformamide and the solution was cooled to 0° C. 1.27 ml (0.01 mol) of N-ethylmorpholine and 1.3 g (0.006 mol) of 1-adamantaneacetyl chloride were added and the mixture was stirred at room temperature for 3 hours. The solvent was removed by evaporation and the residue was dissolved in ethyl acetate/water. The organic solution was washed with 5% citric acid solution, water, 5% sodium bicarbonate solution and brine, dried over magnesium sulphate and evaporated. Chromatography on 60 g of silica gel using ethyl acetate for the elution yielded 0.9 g (29%) of $N^\alpha$-(1-adamantaneacetyl)-$N^\epsilon$-benzyloxycarbonyl-L-lysyl-L-proline isobutylamide as an oil.

Analysis for $C_{35}H_{52}N_4O_5$ (608.83): Calculated: C: 69.05; H: 8.61; N: 9.20%. Found: C: 68.94; H: 8.45; N: 9.14%.

EXAMPLE 5

(A) 14.8 g (0.021 mol) of $N^\alpha$-(1-adamantylsulphonyl)-$N^\epsilon$-phthaloyl-L-lysyl-L-prolyl-L-valinal dimethyl acetal in 75 ml of methanol and a solution of 0.94 g (0.0235 mol) of sodium hydroxide in 75 ml of water were stirred at room temperature for 0.5 hour. The methanol was removed by evaporation, and the solution was diluted with water and extracted with two 50 ml portions of ethyl acetate. The aqueous solution was acidified to pH 2–3 with dilute hydrochloric acid and the oily product was extracted with two 75 ml portions of ethyl acetate. The solution was washed with water, dried over magnesium sulphate and evaporated to give a foam. The foam was taken up in dichloromethane, treated with diethyl ether and cooled, there being obtained 14.4 g (95%) of $N^\alpha$-(1-adamantylsulphonyl)-$N^\epsilon$-(2-carboxybenzoyl)-L-lysyl-L-prolyl-L-valinal dimethyl acetal in the form an an amorphous solid.

(B) 0.5 g (0.0007 mol) of $N^\alpha$-(1-adamantylsulphonyl)-$N^\epsilon$-(2-carboxylbenzoyl)-L-lysyl-L-prolyl-L-valinal dimethyl acetal in 15 ml of dry acetone was treated with 0.5 g of Amberlyst 15 resin and the mixture was stirred at room temperature for 16 hours. The resin was filtered off, washed with 10 ml of acetone and the combined filtrate and washings were evaporated. The resulting oil was chromatographed on 25 g of silica gel using dichloromethane/methanol/acetic acid (190:9:2) for the elution. Evaporation of the eluate followed by trituration of the residue with diethyl ether yielded 0.12 g (26%) of $N^\alpha$-(1-adamantylsulphonyl)-$N^\epsilon$-(2-carboxybenzoyl)-L-lysyl-L-prolylvalinal in the form of an amorphous hygroscopic powder. The product was a mixture of the two epimers.

Analysis for $C_{34}H_{48}N_4O_8S$ (672.84): Calculated: C: 60.69; H: 7.19; N: 8.33%. Found: C: 60.35; H: 7.37; N: 8.03%. C: 60.37; H: 7.21; N: 8.28% (with 0.2 mol of $H_2O$).

EXAMPLE 6

(A) 10 g (0.0148 mol) of $N^\alpha$-(1-adamantylsulphonyl)-$N^\epsilon$-phthaloyl-L-lysyl-L-alanyl-L-valinal dimethyl acetal were treated in sequence with hydrazine hydrate and succinic anhydride/triethylamine in a manner analogous to that described in Example 1(A). The product was purified by chromatography on 150 g of silica gel using chloroform/methanol/acetic acid/water (120:15:3:2) for the elution. After evaporation of the eluate, there were obtained 4.56 g (48%) of $N^\alpha$-(1-adamantylsulphonyl)-$N^\epsilon$-succinyl-L-lysyl-L-alanyl-L-valinal dimethyl acetal in the form of a foam.

(B) 0.5 g (0.78 mmol) of $N^\alpha$-(1-adamantylsulphonyl)-$N^\epsilon$-succinyl-L-lysyl-L-alanyl-L-valinal dimethyl acetal in 10 ml of dimethylformamide and 50 ml of dry acetone was treated with 5 g of Amberlyst 15 resin at room temperature for 28 hours. The mixture was filtered, the resin was washed with dimethylformamide and the filtrate was evaporated to give an oil. Chromatography on 80 g of silica gel using chloroform/methanol/acetic acid/water (120:15:3:2) for the elution followed by lyophilization from aqueous acetic acid yielded 0.3 g (64%) of $N^\alpha$-(1-adamantylsulphonyl)-$N^\epsilon$-succinyl-L-lysyl-L-alanylvalinal as a mixture of epimers.

Analysis for $C_{28}H_{46}N_4O_8S$ (598.76): Calculated: C: 56.17; H: 7.74; N: 9.36%: Found: C: 54.26; H: 7.74; N:

9.02%. C: 54.37; H: 7.85; N: 9.06% (with 1.1 mol of H₂O).

The Nᵅ-(1-adamantylsulphonyl)-Nᵋ-phthaloyl-L-lysyl-L-alanyl-L-valinal dimethyl acetal used as the starting material was prepared as follows:

7.0 g (0.02 mol) of N-benzyloxycarbonyl-L-alanyl-L-valinal dimethyl acetal [prepared in a manner similar to that described in Example 1 (b)] were dissolved in 70 ml of methanol and the solution was hydrogenated for 4 hours in the presence of 0.7 g of 5% palladium/carbon. After removal of the catalyst by filtration, the solvent was removed by evaporation and traces of methanol were removed from the residue by two-fold evaporation with 20 ml of toluene each time. A solution of the residue in 40 ml of dichloromethane was cooled to −20° C. and there were then added 8.53 g (0.018 mol) of Nᵅ-(1-adamantylsulphonyl)-Nᵋ-phthaloyl-L-lysine in 80 ml of dichloromethane followed by 4.45 g (0.0216 mol) of N,N'-dicyclohexylcarbodiimide. The mixture was stirred at −20° C. for 2 hours and left to stand at 4° C. for 16 hours. The separated N,N'-dicyclohexylurea was removed by filtration, the filrate was washed with sodium bicarbonate solution and brine, dried and evaporated. Recrystallization of the residue from methanol yielded 5.1 g (42%) of Nᵅ-(1-adamantylsulphonyl)-Nᵋ-phthaloyl-L-lysyl-L-alanyl-L-valinal dimethyl acetal of melting point 214°–217° C.

Analysis for C₃₄H₅₀N₄O₈S (674.86): Calculated: C: 60.51; H: 7.47; N: 8.30%. Found: C: 60.52; H: 7.40; N: 8.54%.

EXAMPLE 7

(A) 2.2 g (0.0086 mol) of monobenzyl terephthalate in 40 ml of dimethoxyethane/dimethylformamide (1:1) were cooled to 0° C. 0.99 g (0.0086 mol) of N-hydroxysuccinimide and 1.94 g (0.0094 mol) of N,N'-dicyclohexylcarbodiimide were added and the mixture was stirred at 0° C. for 3 hours. The acetate salt of the peptide acetal [prepared from 4 g (0.0057 mol) of Nᵅ-(1-adamantylsulphonyl)-Nᵋ-phthaloyl-L-lysyl-L-valinal dimethyl acetal as described in Example 1 (A)] was dissolved im dimethoxyethane, cooled to 0° C., neutralized with about 1.0 ml of triethylamine and added to the active ester prepared as described above. The mixture was stirred at 0° C. for 1 hour and left to stand overnight at room temperature. The solution was filtered and the filtrate was evaporated. The residue was taken up in ethyl acetate, washed with water and sodium bicarbonate solution, dried over magnesium sulphate and evaporated to give a foam. Chromatography on 70 g of silica gel using ethyl acetate for the elution gave 2.5 g (54%) of Nᵅ-(1-adamantylsulphonyl)-Nᵋ-(4-benzyloxycarbonylbenzoyl)-L-lysyl-L-prolyl-L-valinal dimethyl acetal in the form of a foam.

Analysis for C₄₃H₆₀N₄O₉S (809.04): Calculated: C: 63.84; H: 7.48; N: 6.93%. Found: C: 63.98; H: 7.39; N: 6.91%.

(B) 1.3 g (1.6 mmol) of Nᵅ-(1-adamantylsulphonyl)-Nᵋ-(4-benzyloxycarbonylbenzoyl)-L-lysyl-L-prolyl-L-valinal dimethyl acetal in 15 ml of dimethylformamide were hydrogenated in the presence of 5% palladium/carbon for 3 hours. The catalyst was removed by filtration and the filtrate was evaporated to give an oil. This oil was taken up in sodium bicarbonate solution, extracted with ethyl acetate, the aqueous phase was acidified to pH 2–3 with dilute hydrochloric acid and extracted with ethyl acetate. The organic phase was washed free from acid with water, dried over magnesium sulphate and evaporated to give a foam. This foam was chromatographed on 25 g of silica gel using dichloromethane/methanol/acetic acid (190:9:2) for the elution. Evaporation of the eluate and trituration of the residue with diethyl ether yielded 0.35 g (33%) of Nᵅ-(1-adamantylsulphonyl)-Nᵋ-(4-carboxybenzoyl)-L-lysyl-L-prolyl-L-valinal in the form of a solid.

Analysis for C₃₄H₄₈N₄O₈S (672.84): Calculated: C: 60.69; H: 7.19; N: 8.33%. Found: C: 60.51; H: 7.49; N: 8.60%.

EXAMPLE 8

In a manner analogous to that described in Example 7, but using monobenzyl adipate in place of monobenzyl terephthalate, there was obtained Nᵅ-(1-adamantylsulphonyl)-Nᵋ-adipoyl-L-lysyl-L-prolylvalinal as a mixture of epimers.

Analysis for C₃₂H₅₂N₄O₈S (652.85): Calculated: C: 58.87; H: 8.03; N: 8.58%. Found: C: 57.99; H: 7.95; N: 8.53; H₂O: 1.54%. Water-free: C: 58.89; H: 7.89; N: 8.65%.

EXAMPLE 9

In a manner analogous to that described in Example 7, from monobenzyl terephthalate and Nᵅ-(1-adamantylsulphonyl)-Nᵋ-phthaloyl-L-lysyl-L-alanyl-L-valinal dimethyl acetal there was obtained Nᵅ-(1-adamantylsulphonyl)-Nᵋ-(4-carboxybenzoyl)-L-lysyl-L-alanyl-L-valinal in the form of an amorphous solid.

Analysis for C₃₂H₄₆N₄O₈S (646.81): Calculated: C: 59.42; H: 7.17; N: 8.66%. Found: C: 59.38; H: 7.07; N: 8.73%.

EXAMPLE A

An aerosol composition can contain the following ingredients:

| Ingredient | Percent by weight |
| --- | --- |
| Compound of formula I or salt thereof | 1–5 |
| Ethanol | 15–35 |
| Propellant | ad 100. |

The propellant can be, for example, dichlorodifluoromethane or a 5:1 mixture of 1,2-dichloro-1,1,2,2-tetrafluoroethane and dichlorodifluoromethane.

We claim:

1. A compound of the formula

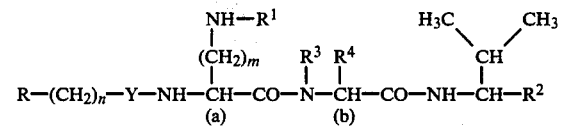

wherein R represents a bridged cycloalkyl group selected from the group consisting of cyclooctyl, cyclodecyl, adamantyl and bicycloheptyl groups, R¹ represents an acyl group derived from an aliphatic or aromatic dicarboxylic acid, R² represents a hydrogen atom or a formyl group, R³ represents a hydrogen atom and R⁴ represents a methyl group or R³ and R⁴ together represent a trimethylene group, Y represents a carbonyl, sulphonyl or methylene group, m stands for an integer of 2 to 6 and n stands for zero, 1 or 2 and wherein the configuration at the carbon atoms designated as (a) and (b) is L, and pharmaceutically acceptable salts thereof.

2. A compound according to claim 1, wherein $R^1$ represents an acyl group derived from an aliphatic dicarboxylic acid containing up to 6 carbon atoms, $R^3$ and $R^4$ together represent a trimethylene group and, when $R^2$ represents a formyl group, the configuration at the carbon atoms to which this group is attached is L.

3. A compound according to claim 1 or claim 2, wherein R represents a monocyclic or bridged cycloalkyl group containing from 6 to 12 carbon atoms.

4. A compound according to any one of claims 1 to 3, wherein $R^1$ represents an acyl group derived from an unsubstituted saturated aliphatic dicarboxylic acid containing up to 6 carbon atoms.

5. A compound according to claim 4, wherein $R^1$ represents a succinyl or adipoyl group.

6. A compound according to claim 1 or claim 3, wherein $R^1$ represents an acyl group derived from an unsubstituted benzenedicarboxylic acid.

7. A compound according to claim 6, wherein $R^1$ represents a 4-carboxybenzoyl group.

8. A compound according to any one of claims 1 to 7, wherein $R^2$ represents a formyl group.

9. A compound according to any one of claims 1 to 8, wherein Y represents a sulphonyl group.

10. A compound according to any one of claims 1 to 9, wherein m stands for 4.

11. A compound according to any one of claims 1 to 10, wherein n stands for zero.

12. The compound $N\alpha$-(1-adamantylsulphonyl)-$N\epsilon$-succinyl-L-lysyl-L-prolyl-L-valinal.

13. The compound $N\alpha$-(1-adamantylsulphonyl)-$N\epsilon$-(4-carboxybenzoyl-L-lysyl-L-prolyl-L-valinal.

14. The compound $N\alpha$-(1-adamantylsulphonyl)-$N\epsilon$-(4-carboxybenzoyl)-L-lysyl-L-alanyl-L-valinal.

15. A compound according to claim 1, selected from the group consisting of:
Nα-(1-adamantylethyl)-$N\epsilon$-succinyl-L-lysyl-L-proline isobutylamide;
Nα-(6,6-dimethylbicyclo-[3.1.1.]heptylethyl)-$N\epsilon$-(γ-glutamyl)-L-lysyl-L-proline isobutylamide and
Nα-(1-adamantaneacetyl)-$N\epsilon$-succinyl-L-lysyl-L-proline isobutylamide.

16. A compound according to claim 1, selected from the group consisting of:
Nα-(1-adamantylsulphonyl)-$N\epsilon$-succinyl-L-lysyl-L-alanylvalinal,
Nα-(1-adamantylsulphonyl)-$N\epsilon$-(2-carboxybenzoyl)-L-lysyl-L-prolylvalinal and
Nα-(1-adamantylsulphonyl)-$N\epsilon$-adipoyl-L-lysyl-L-prolylvalinal.

* * * * *

UNITED STATES PATENT AND TRADEMARK OFFICE
CERTIFICATE OF CORRECTION

PATENT NO.  : 4,623,639

DATED       : November 18, 1986

INVENTOR(S) : HASSALL et al.

It is certified that error appears in the above-identified patent and that said Letters Patent is hereby corrected as shown below:

On the Title Page, "16 Claims" should read -- 17 Claims --.

The following claim should be added:

17. A pharmaceutical composition for the treatment of degenerative diseases and inflammatory conditions associated with elastase-like enzymes containing a therapeutically effective amount of a compound of the formula

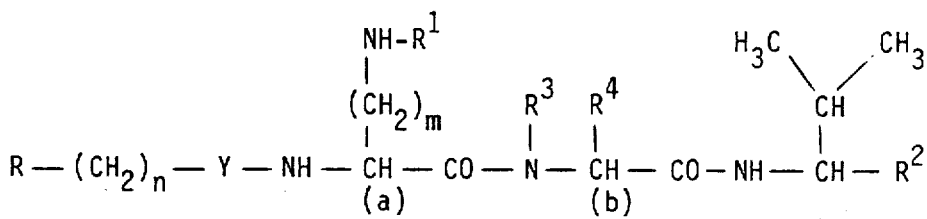

wherein R represents a bridged cycloalkyl group selected from the group consisting of cyclooctyl, cyclodecyl, adamantyl and bicycloheptyl groups, $R^1$ represents an acyl group derived from an aliphatic or aromatic dicarboxylic acid, $R^2$ represents a hydrogen atom or a formyl group, $R^3$ represents a hydrogen atom and $R^4$ represents a

UNITED STATES PATENT AND TRADEMARK OFFICE
CERTIFICATE OF CORRECTION

PATENT NO. : 4,623,639
DATED : November 18, 1986
INVENTOR(S) : HASSALL et al.

It is certified that error appears in the above-identified patent and that said Letters Patent is hereby corrected as shown below:

methyl group or $R^3$ and $R^4$ together represent a trimethylene group, Y represents a carbonyl, sulphonyl or methylene group, m stands for an integer of 2 to 6 and n stands for zero, 1 or 2 and wherein the configuration at the carbon atoms designated as (a) and (b) is L,
and pharmaceutically acceptable salts thereof in combination with a compatible pharmaceutical carrier material.

Signed and Sealed this

Ninth Day of August, 1988

Attest:

DONALD J. QUIGG

Attesting Officer      Commissioner of Patents and Trademarks